(12) United States Patent
Niddam-Hildesheim et al.

(10) Patent No.: US 7,425,628 B2
(45) Date of Patent: Sep. 16, 2008

(54) METHODS FOR THE PURIFICATION OF LEVOFLOXACIN

(75) Inventors: Valerie Niddam-Hildesheim, Even-Yeouda (IL); Neomi Gershon, Rosh Ha-Ain (IL); Eduard Schwartz, Rehovot (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/305,180

(22) Filed: Nov. 27, 2002

(65) Prior Publication Data

US 2003/0144511 A1 Jul. 31, 2003

Related U.S. Application Data

(63) Continuation-in-part of application No. 10/262,965, filed on Oct. 3, 2002, now abandoned, which is a continuation-in-part of application No. 10/263,192, filed on Oct. 3, 2002.

(60) Provisional application No. 60/326,958, filed on Oct. 3, 2001, provisional application No. 60/334,316, filed on Nov. 29, 2001, provisional application No. 60/354,939, filed on Feb. 11, 2002.

(51) Int. Cl.
*C07D 498/06* (2006.01)
(52) U.S. Cl. .................................. 544/101; 544/99
(58) Field of Classification Search ................ 544/101
See application file for complete search history.

(56) References Cited

U.S. PATENT DOCUMENTS

| 4,382,892 | A | 5/1983 | Hayakawa et al. |
| 5,051,505 | A | 9/1991 | Park et al. |
| 5,053,407 | A | 10/1991 | Hayakawa et al. |
| 5,142,046 | A | 8/1992 | Hayakawa et al. .......... 544/105 |
| 5,155,223 | A | 10/1992 | Preiss |
| 5,237,060 | A | 8/1993 | Schriewer et al. .......... 544/101 |
| 5,521,310 | A | 5/1996 | Carretero Gonzalvez et al. .......... 544/101 |
| 5,539,110 | A | 7/1996 | Kim et al. .................... 544/101 |
| 5,545,737 | A | 8/1996 | Sato et al. |
| 6,316,618 | B1 | 11/2001 | Park et al. .................... 544/101 |

FOREIGN PATENT DOCUMENTS

| EP | 0 444 678 B1 | 9/1991 |
| EP | 1 211 254 A1 | 5/2002 |
| WO | WO 00/50428 | 8/2000 |
| WO | WO 03/028664 A | 4/2003 |
| WO | WO 03/028665 A | 4/2003 |

OTHER PUBLICATIONS

Anonymous, "LEVAQUIN", RxList, [online] Dec. 24, 2004, [retrieved on Apr. 2, 2005]. Retrieved from the Internet, <http://www.rxlist.com/cgi/generic/levoflox.htm>.*
Hiroaki Kitaoka, "Effect of Dehydration on the Formaltion of Levofloxacin Pseudopolymorphs," Chem. Pharm. Bull., vol. 43, No. 4 (1995) pp. 649-653.
S. Artula et al, "Pro-and Anti-oxidant Effects of Some Antileprotic Drugs in vitro and Their Influence on Super Oxide Dismutase Activity", ArzneimForsch/Drug Res. 48 (II), Nr. 10 (1998), pp. 1024-1027.
Kang, et al., An Improved Synthesis of Levofloxacin. *Heterocycles*, vol. 45, No. 1, 137-145 (1997).
Opposition dated Jul. 4, 2007 filed by Ratiopharm GmbH in related European Patent No. EP 1 451 194.
Bohm et al., "Kristalle: Asthetich nach außen, regelnaβig nach innen", *Wirkstoffdesign*, 239-240 (1996).
"Common Laboratory Techniques: Crystallization", *Organic Laboratory Manual* (1997) [copy retrieved from web: http://web.archive.org/web/19991003121551/http://www.umsl.edu/~orglab/].
Cross, "Fluoroquinolones", *Seminars in Pediatric Infectious Diseases*, 12(3):211-223 (2001).

* cited by examiner

*Primary Examiner*—Kahsay T Habte
(74) *Attorney, Agent, or Firm*—Kenyon & Kenyon LLP

(57) ABSTRACT

The invention provides a process for preparing levofloxacin hemihydrate, comprising:
(A) dissolving levofloxacin in a solvent selected from the group consisting of acetonitrile, acetonitrile:$H_2O$, dimethyl sulfoxide, dimethyl sulfoxide:$H_2O$, methyl ethyl ketone, methyl ethyl ketone:$H_2O$, butanol, butanol:$H_2O$, and mixtures thereof at an elevated temperature; and
(B) crystallizing levofloxacin hemihydrate.

30 Claims, No Drawings

METHODS FOR THE PURIFICATION OF LEVOFLOXACIN

CROSS-REFERENCE TO RELATED APPLICATIONS

This application is a continuation-in-part application of patent application Ser. No. 10/262,965, filed Oct. 3, 2002, which claims the priority of provisional application serial Nos. 60/326,958, filed Oct. 3, 2001, 60/334,316, filed Nov. 29, 2001 and 60/354,939, filed Feb. 11, 2002, and patent application Ser. No. 10/263,192, filed Oct. 3, 2002. The entire content of each of these applications is incorporated herein by reference.

FIELD OF THE INVENTION

The present invention relates to methods for purifying levofloxacin. In a preferred embodiment, the levofloxacin is prepared with anitoxidants.

BACKGROUND OF THE INVENTION

Levofloxacin is a broad spectrum synthetic antibiotic. Levofloxacin is the S-enantiomer of the racemate, ofloxacin, a fluoroquinolone antimicrobial agent. The antibacterial activity of ofloxacin resides primarily in the S-enantiomer. The mechanism of action of levofloxacin and other fluoroquinolone antimicrobials involves the inhibition of DNA gyrase (bacterial topoisomerase II), an enzyme required for DNA replication, transcription repair and recombination. Levofloxacin is available as LEVAQUIN® which may be orally administered or administered intravenously.

Levofloxacin is a chiral fluorinated carboxyquinolone. Its chemical name is (S)-9-fluoro-2,3-dihydro-3-methyl-10-(4-methyl-1-piperazinyl)-7-oxo-7H-pyrido[1,2,3-de]-1, 4-benzoxazine-6-carboxylic acid CAS Registry No. 100986-85-4). The chemical structure of levofloxacin is shown in Formula I. Unless otherwise indicated, the terms "levofloxacin" and "levofloxacin forms" include the salts, hydrates, solvates and physiologically functional derivatives of levofloxacin. The terms also include all polymorphous forms of levofloxacin to the extent that they are not considered to be salts, hydrates, solvates or physiologically functional derivatives of levofloxacin.

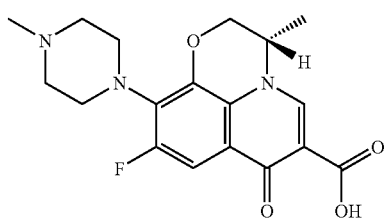

Formula I

U.S. Pat. No. 4,382,892 is directed toward pyrido[1,2,3-de][1,4]benzoxazine derivatives and methods of preparing them.

U.S. Pat. No. 5,053,407 is directed toward optically active pyridobenzoxazine derivatives, processes for preparing the same, and intermediates useful for preparing such derivatives.

U.S. Pat. No. 5,051,505 is directed toward processes for preparing piperazinyl quinolone derivatives. The process comprises reacting dihaloquinolones with piperazine derivatives and tetraalkyl ammonium halides in the presence of a polar solvent such as acetonitrile, dimethylformamide, pyridine, sulfolane and dimethyl sulfoxide.

U.S. Pat. No. 5,155,223 is directed toward the preparation of quinolinecarboxylic acids.

U.S. Pat. No. 5,545,737 discloses selectively producing a levofloxacin hemihydrate or monohydrate by controlling the water content of an aqueous solvent in which levofloxacin is dissolved during a crystallization. Arutla et al., Arzneimittelforschung (October 1998) 48(10):1024-7, asserts that the racemic mixture ofloxacin has an antioxidant property. One disadvantage of the prior art methods for purifying levofloxacin is that they often produce an unsatisfactory yield. For example, 45-65% yields are typical. There remains a need for novel methods for purifying levofloxacin, particularly purified preparations having diminished impurities, such as anti-levofloxacin, desmethyl levofloxacin, N-oxide levofloxacin, desfluoro-levofloxacin and/or decarboxy-levofloxacin.

SUMMARY OF THE INVENTION

The present invention provides novel processes for purifying levofloxacin. Levofloxacin is dissolved in a polar solvent, preferably one selected from the group consisting of DMSO, methyl ethyl ketone, acetonitrile, an alcohol (preferably butanol), a ketone, mixtures thereof, and aqueous mixtures thereof, at an elevated temperature and crystallized to form levofloxacin. In one embodiment, the solvent is anhydrous. In another embodiment, an antioxidant is added, resulting in a more pure levofloxacin product.

DETAILED DESCRIPTION OF THE INVENTION

Crude and semi-pure preparations of levofloxacin can be prepared by methods known in the art. Alternatively, levofloxacin crude can be prepared, for example, by the following method: In a 1-liter reactor equipped with a mechanical stirrer, a condenser and a thermometer, heated at 80° C. is charged 87.5 g (0.31 mole) of (S)-(−)-9,10-difluoro-3-methyl-7-oxo-2,3-dihydro-7H-pyrido[1,2,3-de][1,4]benzoxazine-6-carboxylic acid, 86.3 mL (0.77 mole) of N-methylpiperazine. The slurry is stirred at a rate of 250 rpm under nitrogen atmosphere at 80° C. until completion of the reaction (monitoring by HPLC). Then the slurry is cooled to 75° C. and a mixture of isopropanol (675 mL) and water (25 mL) is added dropwise at this temperature over 2 hours. The slurry is then cooled to 5° C. over 4 hours, maintained at this temperature for 2 hours and filtrated under vacuum at this temperature. The solid is then washed with 175 mL of isopropanol (2 rinses) and dried under vacuum to obtain levofloxacin crude.

In one embodiment of the present invention, crude levofloxacin is purified. As used herein, "purified levofloxacin" is a relative term meaning more pure. As used herein, "crude levofloxacin" refers to levofloxacin that has not undergone a purifying crystallization step. A crude preparation of levofloxacin is mixed with a suitable solvent to form a mixture that is typically a suspension. The temperature of the mixture is then elevated to enhance dissolution of the levofloxacin in the solvent. Typically, the elevated temperature ranges from about 80° C. to about 110° C. Preferably, the mixture is refluxed. Preferably, once the levofloxacin is dissolved in the solvent, the mixture is filtrated while hot. Purified levofloxacin is then precipitated, preferably by slow cooling, and preferably recovered. The purified levofloxacin preferably has a purity of about 99% or greater, more preferably about 99.5% or greater.

Polar solvents are generally suitable. Preferably, the solvent is DMSO, methyl ethyl ketone, butanol, acetonitrile, mixtures thereof, or aqueous mixtures thereof. As used herein, the term "polar solvent" is intended as a relative term to mean relatively more polar than another solvent.

The solvent may be anhydrous or may contain a small amount of water. The solvent preferably contains water when a water-soluble antioxidant, such as sodium metabisulfite, is used. The amount of water should be less than about 20% (v/v) and preferably about 10% (v/v) or less. Greater amounts of water tends to decrease the yield. n-BuOH:$H_2O$ (9:1) and acetonitrile:$H_2O$ (99:1) are examples of suitable water-containing solvents. Acetonitrile and acetonitrile:$H_2O$ (99:1) are the most preferred solvents for purifying levofloxacin.

In another embodiment, an antioxidant is added to the mixture prior to precipitation. The antioxidant may be any that prevents the formation of N-oxide levofloxacin, particularly during crystallization. Examples include ascorbic acid, sodium ascorbate, calcium ascorbate, ascorbic palmitate, butylated hydroxyanisole, butylated hydroxytoluene, 2,4,5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone, tocopherols (such as vitamin E), and pharmaceutically acceptable salts and mixtures thereof. Preferably, the antioxidant includes sodium metabisulfite or ascorbic acid.

An antioxdiant, if used, can be added at various points in the purification process. For example, in one embodiment, an antioxidant is admixed with levofloxacin before or during the crystallization step or before the dissolution step. In another embodiment, an antioxidant is admixed with (S)-(−)-9,10-Difluoro-3-Methyl-7-oxo-2,3-Dihydro-7H-Pyrido[1,2,3-de][1,4]Benzoxazine-6-Carboxylic Acid, a levoflaxacin precursor, prior to its conversion to levofloxacin at an elevated temperature.

The amount of antioxidant, when present, is preferably about 0.2% to about 5% by weight, more preferably about 0.2% to about 1%.

The function and advantages of these and other embodiments of the present invention will be more fully understood from the examples below. The following examples are intended to illustrate the benefits of the present invention, but do not exemplify the full scope of the invention.

EXAMPLES

The following Table 1 summarizes the results of the experiments described in the Examples below. The percentage of each component in Table 1 was determined by HPLC using a method based on the European Pharmacopea method for related substances in Ofloxacin.

TABLE 1

Purification During Crystallization

| | | Impurity Profile | | | | | | |
| --- | --- | --- | --- | --- | --- | --- | --- | --- |
| | | Crude | | | | Purified | | |
| Ex. | Solvent System | Levo | Imp. D Anti | Imp. E DesMe | Imp. F N-Oxide | Levo | Imp. D Anti | Imp. E DesMe | Imp. F N-Oxide |
| 1 | n-Bu—OH | 99.44 | ND | 0.11 | 0.19 | 99.60 | ND | 0.09 | 0.19 |
| 2 | n-BuOH Asc. acid (2.4%) | 99.58 | ND | 0.11 | 0.21 | 99.78 | ND | 0.08 | ND |
| 3 | n-BuOH/ $H_2O$ $Na_2S_2O_5$ (0.6%) | 99.58 | ND | 0.11 | 0.21 | 99.85 | ND | 0.08 | ND |
| 4 | ACN | 99.44 | ND | 0.11 | 0.19 | 99.67 | ND | 0.04 | 0.15 |
| 5 | ACN:$H_2O$ | 99.64 | 0.08 | 0.09 | <0.03 | 99.85 | ND | 0.06 | <0.03 |
| 6 | ACN:$H_2O$ $Na_2S_2O_5$ (0.2%) | 99.77 | <0.03 | 0.05 | <0.03 | 99.93 | ND | <0.03 | ND |
| 7 | ACN $Na_2S_2O_5$ (0.5%) | 99.58 | ND | 0.11 | 0.21 | 99.70 | ND | 0.06 | 0.1 |
| 8 | DMSO:$H_2O$ | 99.44 | ND | 0.11 | 0.19 | 99.75 | ND | 0.06 | 0.13 |
| 9 | MEK | 99.44 | ND | 0.11 | 0.19 | 99.58 | ND | ND | 0.26 |
| 10 | ACN:$H_2O$ (90:10) $Na_2S_2O_5$ (0.5%) | 99.58 | ND | 0.11 | 0.21 | 99.69 | ND | 0.08 | ND |
| 11 | ACN:$H_2O$ (95:5) $Na_2S_2O_5$ (0.5%) | 99.58 | ND | 0.11 | 0.21 | 99.74 | ND | 0.06 | ND |
| 12 | ACN:$H_2O$ (95:5) $Na_2S_2O_5$ (0.25%) | 99.58 | ND | 0.11 | 0.21 | 99.81 | ND | 0.08 | ND |
| 13 | DMSO Asc. Acid (0.6%) | 99.80 | ND | 0.03 | 0.02 | — | — | — | — |

TABLE 1-continued

Purification During Crystallization

| | | Impurity Profile | | | | | | |
|---|---|---|---|---|---|---|---|---|
| | | Crude | | | | Purified | | |
| Ex. | Solvent System | Levo | Imp. D Anti | Imp. E DesMe | Imp. F N-Oxide | Levo | Imp. D Anti | Imp. E DesMe | Imp. F N-Oxide |
| 14 | DMSO Na$_2$S$_2$O$_5$ (0.5 eq.) | 99.77 | 0.04 | 0.10 | <0.03 | — | — | — | — |

ND = Not detected.

Example 1 n-BuOH 1 g of levofloxacin crude was put in suspension in 7 ml of n-BuOH. The mixture was heated to reflux temperature until complete dissolution of the material. Then the solution was cooled to RT over a period of 2.5 hours. The precipitate was filtered under vacuum, washed with n-BuOH and dried at 60° C. in a vacuum oven to give 810 mg (81%) of purified levofloxacin hemihydrate.

Example 2 n-BuOH/Ascorbic acid 1.5 g of levofloxacin crude and 36 mg of ascorbic acid were put in suspension in 9.5 ml of n-BuOH under inert atmosphere. The mixture was heated to reflux temperature and a hot filtration was performed. The solution was then evaporated to dryness and n-BuOH (10 ml) was added. The mixture was heated to reflux until complete dissolution and then cooled to RT over a period of 1.5 hour. The precipitate was filtered under vacuum, washed with n-BuOH (4 ml) and dried at 60° C. in a vacuum oven to give 840 mg (56%) of purified levofloxacin hemihydrate.

Example 3 n-BuOH:H$_2$O (9:1)/Metabisulfite 1.5 g of levofloxacin crude and 10 mg of sodium metabisulfite were put in suspension in 6 ml of a mixture n-BuOH:H$_2$O (9:1) under nitrogen atmosphere. The mixture was heated to reflux temperature until complete dissolution of the material. Then the solution was cooled to RT over a period of 1.5 hours. The precipitate was filtered under vacuum, washed with a mixture n-BuOH:H$_2$O (9:1) (4 ml) and dried at 60° C. in a vacuum oven to give 1.2 g (81%) of purified levofloxacin hemihydrate. The purified levofloxacin hemihydrate contained virtually no N-oxide levofloxacin.

Example 4

ACN 1.5 g of levofloxacin crude was put in suspension in 10.5 ml of ACN. The mixture was heated to reflux temperature until complete dissolution of the material. Then the solution was cooled to 0° C. over a period of 20 minutes. The precipitate was filtered under vacuum, washed with ACN (1.5 ml) and dried at 30° C. in a vacuum oven to give 1.15 g (77%) of purified levofloxacin (hemihydrate/monohydrate mixture). The purified levofloxacin contained approximately half the amount of desmethyl levofloxacin as that in the crude sample.

Example 5

ACN:H$_2$O (99:1)

25 g of wet levofloxacin crude (about 22.17 g or dry levofloxacin) was put in suspension in 225 mL of mixture ACN:H$_2$O (99:1) under nitrogen atmosphere. The mixture was heated to reflux during 1 hour and then filtrated under vacuum with Hyflow when still hot. Then the solution was heated again to reflux and cooled to 0° C. over a period of 1 hour. The precipitate was filtrated under vacuum, washed with ACN:H$_2$O (2×12 mL) and dried in a vacuum oven to give 18.6 g (84%) of purified levofloxacin hemihydrate. The purified levofloxacin hemihydrate contained approximately one-third less desmethyl levofloxacin than in the crude sample.

Example 6

ACN:H$_2$O (99:1)/Metabisulfite 8 g of wet levofloxacin crude (about 5.6 g of dry levofloxacin) and 14 mg of sodium metabisulfite were put in suspension in 39 ml of a mixture ACN:H$_2$O (99:1) under nitrogen atmosphere. The mixture was heated to reflux during 1 hour, 0.65 g of Hyflo was added and the reflux was continued for an additional half an hour. The mixture was filtrated under vacuum when still hot. Then the solution was cooled to 3° C. over a period of 30 minutes. The precipitate was filtrated under vacuum, washed with a mixture ACN:H$_2$O (99:1) (5 ml) and dried at 60° C. in a vacuum oven to give 1.77 g (31%) of purified levofloxacin. Technical problems during the hot filtration decreased the yield.

Example 7

ACN/Metabisulfite 1.5 g of levofloxacin crude and 8 mg of sodium metabisulfite were put in suspension in 10.5 ml of ACN under nitrogen atmosphere. The mixture was heated to reflux temperature and a hot filtration was performed. Then the solution was heated again to reflux temperature until complete dissolution of the material. The solution was then cooled to 0° C. over a period of 30 minutes. The precipitate was filtrated under vacuum and dried at 60° C. in a vacuum oven to give 1.04 g (69%) of purified levofloxacin. The purified levofloxacin contained approximately half the amount of N-oxide levofloxacin as that in the crude sample.

Example 8

DMSO/H₂O 1 g of levofloxacin crude was put in suspension in 1.5 ml of DMSO. The mixture was heated to 108° C. until complete dissolution of the material. Then H$_2$O (7.5 ml) was added over 10 minutes and the mixture was cooled to RT. The precipitate was filtrated under vacuum, washed with 1 ml of a mixture DMSO:H$_2$O 1:5 and dried at 60° C. in an air-flow oven to give 840 mg (84%) of purified levofloxacin hemihydrate.

Example 9

MEK 1.5 g of levofloxacin crude was put in suspension in 15 ml of MEK. The mixture was heated to reflux temperature until complete dissolution of the material. Then the solution was cooled to −5° C. over a period of 3 hours. The precipitate was filtrated under vacuum, washed with 1.5 ml of MEK and dried at 30° C. in a vacuum oven to give 840 mg (84%) of purified levofloxacin hemihydrate.

Example 10

ACN:H2O (9:1)/Metabisulfite 1.5 g of levofloxacin crude and 8 mg of sodium metabisulfite were put in suspension in 10.5 ml of a mixture ACN:H$_2$O 9:1 under nitrogen atmosphere. The mixture was heated to reflux temperature until complete dissolution of the material. Then the solution was cooled to RT over a period of 30 minutes. The precipitate was filtrated under vacuum, washed with a mixture ACN:H$_2$O 9:1 (4 ml) and dried at 60° C. in a vacuum oven to give 1.16 g (77%) of pure levofloxacin.

Example 11

ACN:H2O (95:5)/Metabisulfite (8 mg)

1.5 g of levofloxacin crude and 8 mg of sodium metabisulfite were put in suspension in 10.5 ml of a mixture ACN:H$_2$O 95:5 under nitrogen atmosphere. The mixture was heated to reflux temperature and a hot filtration was performed. The solution was heated again to reflux temperature then cooled to 3° C. in 30 minutes. The precipitate was filtrated under vacuum and dried at 60° C. in a vacuum oven to give 500 mg (33%) of pure levofloxacin.

Example 12

ACN:H2O (95:5)/Metabisulfite (4 mg)

1.5 g of levofloxacin crude and 4 mg of sodium metabisulfite were put in suspension in 15 ml of a mixture ACN:H$_2$O 95:5 under nitrogen atmosphere. The mixture was heated to reflux temperature until complete dissolution of the material. Then the solution was cooled to 3° C. over a period of 2 hours. The precipitate was filtrated under vacuum and dried at 60° C. in a vacuum oven to give 1.3 g (86.7%) of pure Levofloxacin.

Example 13

DMSO/Ascorbic Acid

In a three necks flask equipped of a condenser were put in suspension in 3.5 ml of DMSO at 80° C. under nitrogen atmosphere 5 g (17.8 mmol) of (S)-(−)-9,10-Difluoro-3-Methyl-7-oxo-2,3-Dihydro-7H-Pyrido[1,2,3-de][1,4]Benzoxazime-6-Carboxylic Acid, 44.6 g (44.6 mmol), 31 mg (0.17 mmol) of ascorbic acid. The reaction mixture was heated at this temperature (4h30) until completion of the reaction. Then the solution was cooled to 70° C. and IPA (40 ml) was added dropwise. The mixture was cooled to 0° C. in 1 hour and then stirred at this temperature for 30 minutes. The precipitate was filtrated under vacuum, washed with IPA (10 ml) and dried at 60° C. in a vacuum oven to give 5.63 g (87.6%) of pure levofloxacin.

Example 14

DMSO/Metabisulfite

In a three necks flask equipped of a condenser were put in suspension in 7 ml of DMSO at 80° C. under nitrogen atmosphere 10 g (35.5 mmol) of (S)-(−)-9,10-Difluoro-3-Methyl-7-oxo-2,3-Dihydro-7H-Pyrido[1,2,3-de][1,4]Benzoxazime-6-Carboxylic Acid, 9.0 g (90mmol), 34 mg (0.17 mmol) of sodium metabisulfite. The reaction mixture was heated at this temperature (5h30) until completion of the reaction. Then the solution was cooled to 70° C. and IPA (40 ml) was added dropwise. The mixture was cooled to 0° C. in 1 hour and then stirred at this temperature for 30 minutes. The precipitate was filtrated under vacuum, washed with IPA (10 ml) and dried at 60° C. in a vacuum oven to give 11.8 g (92.4%) of pure levofloxacin.

What is claimed is:
1. A process for preparing levofloxacin, comprising:
dissolving levofloxacin in a solvent selected from the group consisting of acetonitrile, acetonitrile:H$_2$O, dimethyl sulfoxide, dimethyl sulfoxide:H$_2$O, anhydrous methyl ethyl ketone and anhydrous butanol at an elevated temperature, wherein when the solvent is methyl ethyl ketone or butanol, no water is added; and
crystallizing levofloxacin.
2. The process of claim 1, wherein the at least one solvent comprises acetonitrile:H$_2$O in a ratio of about 90:10, acetonitrile:H$_2$O in a ratio of about 95:5 or acetonitrile:H$_2$O in a ratio of about 99:1.
3. The process of claim 2, wherein the at least one solvent comprises acetonitrile:H$_2$O in a ratio of about 99:1.
4. The process of claim 1, wherein the elevated temperature is greater than about 80° C. and less than about 110° C.
5. The process of claim 1, wherein the dissolution step comprises refluxing the at least one solvent.
6. The process of claim 1, further comprising drying the crystallized levofloxacin at about 60° C.
7. The process of claim 1, wherein the at least one solvent comprises acetonitrile:H$_2$O.
8. The process of claim 1, wherein the at least one solvent comprises dimethyl sulfoxide:H$_2$O.
9. The process of claim 8, wherein the at least one solvent comprises dimethyl sulfoxide:H$_2$O in a ratio of about 1:5.
10. The process of claim 1, wherein the at least one solvent comprises anhydrous butanol.
11. The process of claim 1, wherein the at least one solvent comprises acetonitrile.

12. The process of claim 1, wherein the at least one solvent comprises dimethyl sulfoxide.

13. The process of claim 1, wherein the at least one solvent comprises anhydrous methyl ethyl ketone.

14. The process of claim 1, wherein the at least one solvent comprises acetonitrile, dimethyl sulfoxide, anhydrous methyl ethyl ketone or anhydrous butanol.

15. The process of claim 1, further comprising (a) mixing an antioxidant with levofloxacin before the dissolving step, (b) adding an antioxidant during the dissolving step, (c) adding the antioxidant between the dissolving step and crystallizing step, or (d) adding an antioxidant during the crystallizing step.

16. The process of claim 15, wherein the antioxidant used in (a), (b), (c) or (d) ranges from about 0.2% to about 5% by weight of the levofloxacin used in the dissolving step.

17. The process of claim 15, wherein the antioxidant is mixed with the levofloxacin before the dissolving step.

18. The process of claim 15, wherein the antioxidant is added during the crystallization step.

19. The process of claim 1, wherein the crystallized levofloxacin has a purity of about 99% or greater.

20. The process of claim 1, wherein the crystallized levofloxacin has a purity of about 99.5% or greater.

21. The process of claim 1, wherein the at least one solvent comprises acetonitrile:$H_2O$ in a ratio of about 95:5.

22. The process of claim 4, wherein the at least one solvent comprises acetonitrile:$H_2O$ in a ratio of about 99:1.

23. A process for preparing levofloxacin, comprising:
dissolving levofloxacin in at least one solvent selected from the group consisting of acetonitrile, acetonitrile:$H_2O$, dimethyl sulfoxide, dimethyl sulfoxide:$H_2O$ and mixtures thereof at an elevated temperature; and
crystallizing levofloxacin.

24. A process for preparing levofloxacin hemihydrate, comprising
dissolving levofloxacin in butanol at an elevated temperature; and
crystallizing levofloxacin hemihydrate,
wherein the process also includes step (a), (b), (c) or (d); (a) mixing an antioxidant with levofloxacin before the dissolving step, (b) adding an antioxidant during the dissolving step, (c) adding an antioxidant between the dissolving step and crystallizing step, or (d) adding an antioxidant during the crystallizing step.

25. The process of claim 24, wherein the antioxidant used in (a), (b), (c) or (d) ranges from about 0.2% to about 5% by weight of the levofloxacin used in the dissolving step.

26. The process of claim 24, wherein the antioxidant is mixed with the levofloxacin before the dissolving step.

27. The process of claim 24, wherein the antioxidant is added during the crystallization step.

28. The process of claim 24, further comprising mixing water with the n-butanol in the dissolving step.

29. The process of claim 28, wherein the mixture of n-butanol and water has water at about 10% or less by volume.

30. The process of claim 29, wherein the mixture of n-butanol and water has a volume ratio of 9:1.

* * * * *